Nov. 16, 1965 P. A. CLARKE Plant Pat. 2,572
CHERRY TREE
Filed July 23, 1964
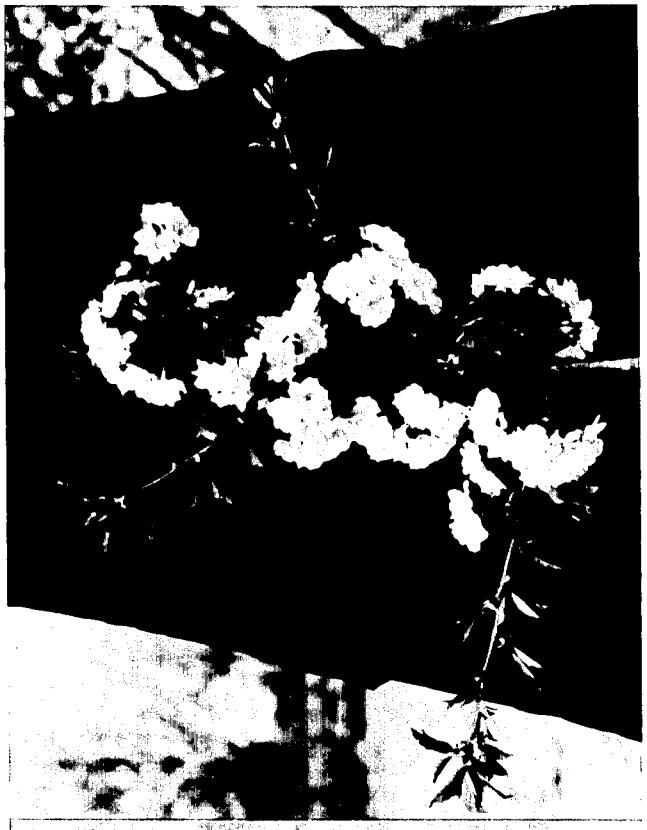
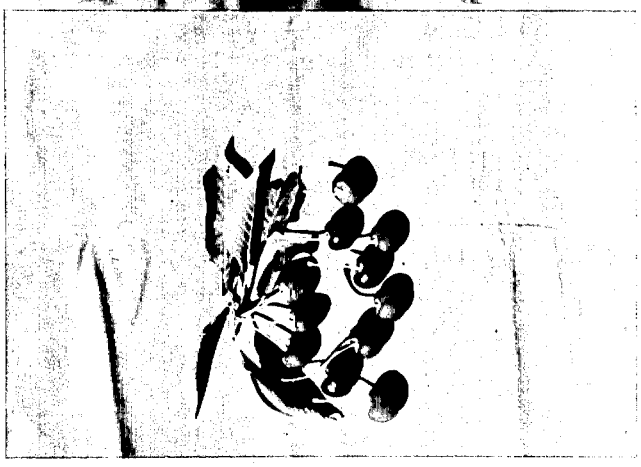
Inventor.
Percy A. Clarke
By: Robbs & Robbs
Attorneys.

United States Patent Office

Plant Pat. 2,572
Patented Nov. 16, 1965

2,572
CHERRY TREE

Percy A. Clarke, Walla Walla, Wash., assignor to Stark Bro's Nurseries & Orchards Company, Louisiana, Mo., a corporation of Missouri Filed July 23, 1964, Ser. No. 384,816
1 Claim. (Cl. Plt.—37)

The present invention relates to a new and distinct variety of cherry tree which was discovered by me as a whole tree bud sport of the cherry variety known as "Bing" (unpatented).

At the time of my discovery aforementioned, I was growing a block of "Bing" cherry trees in my orchard near Walla Walla, Washington, and my attention was attracted to one particular tree in this block during one of my routine inspections of the orchard. I observed that the flowers on this particular tree were entirely different from the normal flowers of the "Bing" variety, as evidenced by the fact that the flowers were quite large in size, double in form and extremely ornamental, contrary to the single type flowers of the regular "Bing" variety which is much less showy and unsuitable as an ornamental variety.

On making this discovery, I promptly took steps to preserve the sport, keep it under close observation, and to asexually reproduce the same by budding. These observations and tests convinced me that the new sport is a completely new and distinct variety, although except for the highly ornamental flowers thereof, the other general characteristics of the tree and fruit are similar to the "Bing" variety.

Asexual reproduction of the new variety, as performed by budding at Walla Walla, Washington, shows that the foregoing characteristics and distinctions come true and are established and transmitted through succeeding propagations.

The accompanying drawing shows typical specimens of the flowers, foliage and fruit of my new variety as depicted in color as nearly true as it is reasonably possible to make the same in a color illustration of this character, with certain of the fruit specimens being shown in typical clusters as borne on the tree, and with other fruit specimens shown individually.

The following is a detailed description of my new variety, with color terminology in accordance with Ridgway's Color Standards and Nomenclature, except where general color terms of ordinary dictionary significance are obvious:

Locality where grown and observed: Near Walla Walla, Washington.

Dates of first and last pickings: About the last week of June and the first week of July, respectively.

Tree: Medium-large size; medium-vigorous; open; spreading; round-topped; hardy; productive; regular bearer.

*Trunk.*—Medium-stocky; medium-smooth.

*Branches.*—Medium-stocky; smooth; dull. Color—Liver Brown, Plate XIV, color No. 7′, tone M.

*Lenticels.*—Few; small.

*Leaves.*—Medium-large size; obovate; acutely pointed; medium thickness; smooth. Length — about 4½ inches. Width—about 2¼ inches. Color—Elm Green, Plate XVII, color No. 27′. tone M. Margin — coarsely serrate. Petiole — medium-long; medium thickness. Glands—usually average 2 in number; alternate; medium size; globose; appressed; glabrous.

Flowers: Medium-early in comparison with other varieties grown in the same area; very large; double, with 3 or more layers of petals.

*Dates of first and full bloom.*—About April 10 and April 16, respectively.

*Color.*—White.

Fruit:

*Maturity when described.*—Eating ripe (first week in July).

*Size.*—Variable; medium large.

*Form.*—Uniform; symmetrical; globose; sides unequal.

*Suture.*—An inconspicuous line extending over entire circumference, but discontinues at apex.

*Ventral surface.*—Rounded.

*Cavity*—Rounded; suture showing on one side. Depth — medium. Breadth — medium. Markings—none.

*Base.*—Rounded.

*Stem.*—Medium slender; glabrous; medium strong adherence to stone; about 1½ inches long.

*Skin.*—Thick; some tendency to break. Color — High Red Blush corresponding to Maroon, Plate I, color No. 3, tone M when fully ripe.

*Flesh.*—Color—Oxblood Red, Plate I, color No. 1, tone K when fully ripe. Amygdalin—moderate. Juice — moderate quantity. Texture — firm. Fibres — few; coarse. Ripens — fairly evenly. Flavor — sub-acid. Aroma — distinct. Eating quality—good.

Stone: Semi-free.

*Fibres.*—Free.

*Size.*—Medium small. Length — about 7/16 inch. Thickness—about ⅜ inch.

*Form.*—Ovoid; full.

*Base.*—Oblique.

*Hilum.*—Broadly oblong.

*Apex.*—Rounded.

*Sides.*—Unequal; curved on left side.

*Surface.*—Irregularly furrowed near base.

*Ridges.*—Rounded toward base.

*Pits.*—None.

*Dorsal edge.*—Continuous.

Use: Fruit useful for market, dessert, culinary, canning, and flowers highly ornamental.

Keeping quality: Medium good.

Shipping quality: Good.

I claim:

A new and distinct variety of cherry tree, substantially as herein shown and described, characterized particularly as to novelty by the general similarity of the tree and fruit to the tree and fruit of the variety known as "Bing" (unpatented), but being essentially differentiated from that variety by its habit of bearing white flowers of large size and double form which are especially attractive for ornamental purposes as compared with the single type flowers of "Bing" variety, which is less showy and unsuitable as an ornamental variety.

No references cited.

ABRAHAM G. STONE, *Primary Examiner.*